(12) United States Patent
Sato et al.

(10) Patent No.: US 8,488,853 B2
(45) Date of Patent: Jul. 16, 2013

(54) X-RAY IMAGING APPARATUS

(75) Inventors: Naotaka Sato, Tochigi-ken (JP); Shingo Abe, Tochigi-ken (JP); Yoshinori Shimizu, Tochigi-ken (JP); Kunio Shiraishi, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 250 days.

(21) Appl. No.: 13/117,336

(22) Filed: May 27, 2011

(65) Prior Publication Data
US 2011/0293164 A1    Dec. 1, 2011

(30) Foreign Application Priority Data
May 28, 2010    (JP) .................................. 2010-123524

(51) Int. Cl.
*G06K 9/00*    (2006.01)
(52) U.S. Cl.
USPC ............................... 382/128; 128/922; 378/4
(58) Field of Classification Search
USPC .. 382/100, 128, 129, 130, 131, 132; 128/922; 378/4–27
See application file for complete search history.

(56) References Cited

U.S. PATENT DOCUMENTS

| | | | | |
|---|---|---|---|---|
| 4,709,385 A * | 11/1987 | Pfeiler et al. | ............... | 378/98.12 |
| 5,285,786 A * | 2/1994 | Fujii | ............... | 600/425 |
| 5,644,613 A * | 7/1997 | Mick | ............... | 378/98.12 |
| 5,712,895 A * | 1/1998 | Negrelli et al. | ............... | 378/207 |
| 5,982,915 A * | 11/1999 | Doi et al. | ............... | 382/130 |
| 7,412,023 B2 * | 8/2008 | Ohishi et al. | ............... | 378/4 |
| 8,175,357 B2 * | 5/2012 | Ozawa | ............... | 382/130 |
| 8,355,557 B2 * | 1/2013 | Chen et al. | ............... | 382/132 |
| 2005/0025365 A1 * | 2/2005 | Oosawa | ............... | 382/218 |
| 2006/0239530 A1 * | 10/2006 | Oosawa | ............... | 382/130 |
| 2008/0205591 A1 * | 8/2008 | Ozawa | ............... | 378/44 |
| 2010/0092061 A1 * | 4/2010 | Chen et al. | ............... | 382/132 |

FOREIGN PATENT DOCUMENTS
JP    2003-143479    5/2003

* cited by examiner

*Primary Examiner* — Anand Bhatnagar
(74) *Attorney, Agent, or Firm* — Oblon, Spivak, McClelland, Maier & Neustadt, L.L.P.

(57) ABSTRACT

An X-ray imaging apparatus is configured to subtract a first X-ray image from a second X-ray image to generate a first subtraction image showing information on a blood vessel, calculate an amount of pixel shift between the first X-ray image and the third X-ray image, subtract the first X-ray image from the third X-ray image to generate a second subtraction image showing information on an insertion instrument, and combine the first subtraction image with the second subtraction image to generate a synthetic image by performing a pixel shift correction based on the amount of pixel shift.

8 Claims, 14 Drawing Sheets

X-RAY IMAGING APPARATUS

CROSS-REFERENCE TO RELATED APPLICATIONS

This application is based upon and claims the benefit of priority from Japanese Patent Application No. 2010-123524, filed May 28, 2010, the entire contents of which are incorporated herein by reference.

FIELD

Embodiments described herein relate generally to an X-ray imaging apparatus configured to capture an X-ray image.

BACKGROUND

An X-ray imaging apparatus irradiates X-rays to an object and performs fluoroscopy of the object by detecting the X-ray. The X-ray imaging apparatus is becoming pervasive. Under medical treatment in a blood vessel using the X-ray imaging apparatus, especially in a head region where the structure of the blood vessel is complicated, when a doctor sees the perspective image obtained by the fluoroscopy, a fluoroscopy roadmap, in which previously captured blood vessel image is combined with the perspective images to show combined images as a guide for the blood vessel, is widely used.

Fluoroscopy subtraction is known as one of the fluoroscopy roadmap. In the fluoroscopy subtraction, subtraction between the perspective images and a blood vessel image, etc. is performed to show a catheter or a guide wire, etc. in black in the image where the blood vessel is shown in white and a background (e.g., a bone) is deleted. In the fluoroscopy subtraction, a blood vessel image is generated by injecting contrast agents into the target blood vessel and performing fluoroscopy or capturing images. Next, a subtraction image is generated by performing, for example, subtraction between the perspective image, which can be obtained by fluoroscopy, and the blood vessel image. The generated subtraction image does not have a background (e.g., a bone) and have the blood vessel image. A doctor manipulates a catheter or a guide wire, etc., while checking a blood vessel using the subtraction image.

The fluoroscopy subtraction is indispensable to today's medical treatment with the spread of the medical treatment using a catheter in a blood vessel. Thus, various methods for generating a subtraction image have been proposed (see, Japanese Patent Publication (Kokai) No. 2002-199279).

In the above mentioned subtraction image, a background, such as a bone, which appears in a perspective image and a blood vessel image in common, disappears, and the blood vessel and the insertion instrument (e.g., a catheter inserted in an object), is displayed as a difference image. However, when the object moves in manipulation (e.g., by motion), the background position captured in the perspective image moves, and thus the moved background is displayed on a subtraction image. The object appearing in a subtraction image due to, for example, the motion of the object is called a "motion artifact." The motion artifact hinders doctor's manipulation.

In order to reduce the motion artifact captured in the subtraction image, a blood vessel image can be recaptured for the moved object to show a subtraction image using the recaptured blood vessel image. However, the recaptured blood vessel image causes an increase in the amount of X-ray irradiation.

DETAILED DESCRIPTION

Embodiments of an X-ray imaging apparatus configured to capture an X-ray image according to the present invention will be described below with reference to the views of the accompanying drawings.

Figure 1:
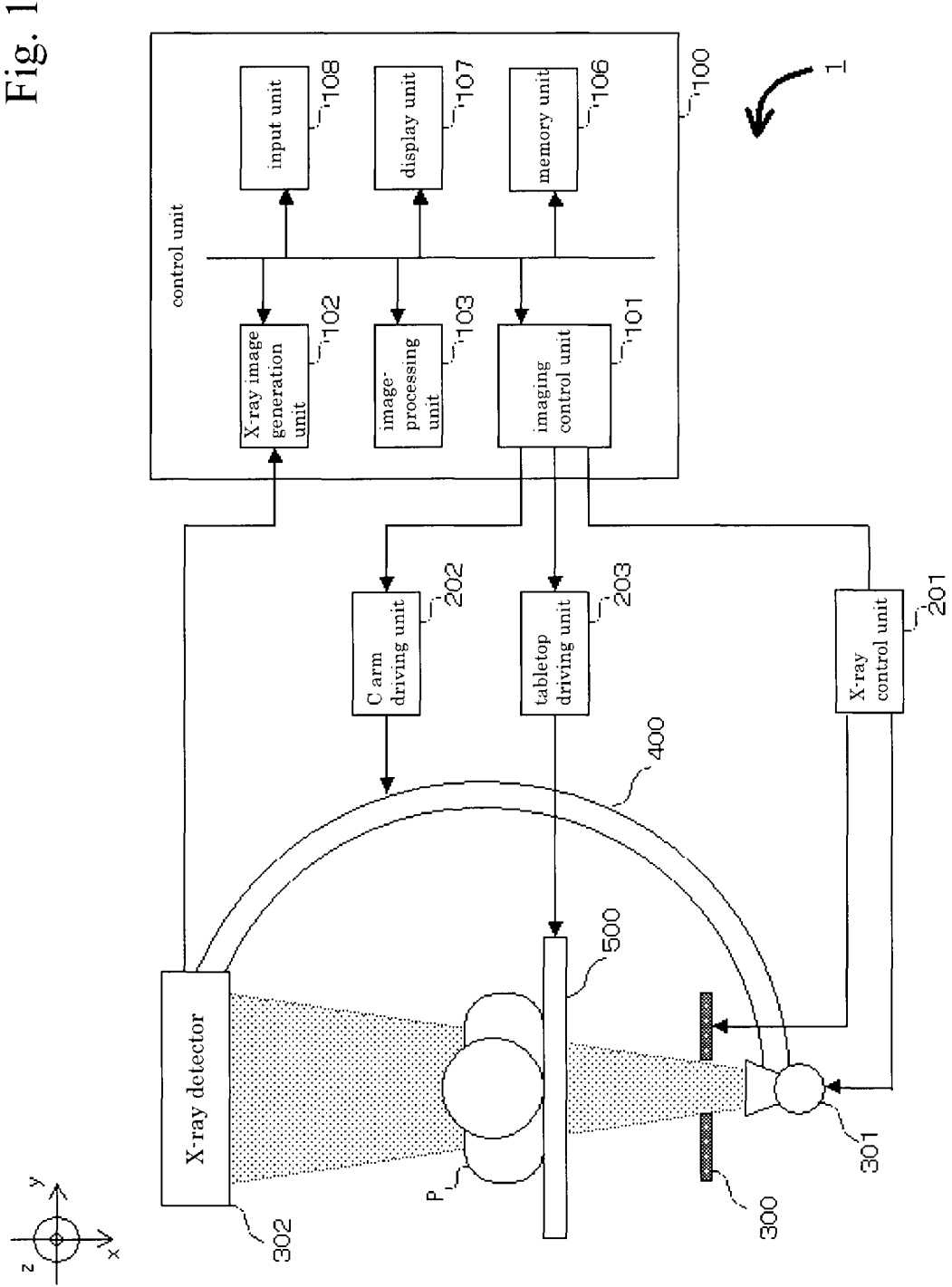
FIG. 1 is a block diagram showing a structure of an X-ray imaging apparatus according to the first embodiment of the present invention.

FIG. 1 is a block diagram showing a structure of an X-ray imaging apparatus according to the first embodiment of the present invention.

A control unit 100 comprises a CPU (Central Processing Unit), a ROM (Read Only Memory) and a RAM (Random Access Memory). The control unit 100 comprises an imaging control unit 101, an X-ray image generation unit 102, an image-processing unit 103, a memory unit 106, a display unit 107 and an input unit 108.

The control unit 100 controls overall of the X-ray imaging apparatus 1 by processing signals supplied from each unit, generating various control signals, and supplying the generated signals.

The imaging control unit 101 outputs various control signals to an X-ray control unit 201, a C arm driving unit 202 and a tabletop driving unit 203, when the X-ray imaging apparatus 1 captures a mask image and a live image (described below). Specifically, the imaging control unit 101 outputs an X-ray beam irradiation signal for irradiating X-rays to an X-ray tube 301 and a collimator moving signal for moving the collimator and changing the X-ray irradiation range to the X-ray control unit 201. Further, the imaging control unit 101 outputs, to the C arm driving unit 202, a C arm driving signal for moving a C arm 400 and changing an imaging position. Moreover, the imaging control unit 101 outputs a tabletop driving signal for moving a tabletop 500 to the tabletop driving unit 203.

The X-ray image generation unit 102 generates a transmission image (hereinafter, an "X-ray image" refers to the image generated based on the X-ray detection signal) based on the X-ray detection signal output from an X-ray detector 302, when the X-ray detector 302 detects X-rays. The X-ray image generation unit 102 outputs an X-ray image to the display unit 107 or the memory unit 106.

The image-processing unit 103 reads out the X-ray image stored in the memory unit 106 and performs image processing, such as subtraction processing or pixel shift processing for the X-ray image.

When the image-processing unit 103 performs the subtraction processing, the image-processing unit 103 extracts pixel values assigned to the corresponding coordinates and calculates differences of pixel values between two X-ray images read out by the image-processing unit 103. Then, the image-processing unit 103 performs a mapping of the difference values on the coordinates in which the pixel values are extracted.

By performing the calculation and mapping of the differences of the pixel values for each pixel, the image-processing unit 103 performs the subtraction processing. By this subtraction processing, the X-ray image showing the difference between two images is substantially obtained. In this embodiment, the subtraction processing is described to calculate the differences of the pixel values assigned to the corresponding coordinates, but the invention is not limited to this. The pixel values of the coordinates matched by arbitrary methods may be processed as the subtraction processing in a similar way.

When the image-processing unit 103 performs the pixel shift processing, the image-processing unit 103 extracts pixel values assigned to a certain coordinate and performs a mapping of the extracted pixel values from the coordinate before moving to the other coordinate after moving in an arbitrary direction. By performing extraction and mapping the pixel values for each pixel, the image-processing unit 103 performs the pixel shift processing. By the pixel shift processing, the X-ray image, which moves in the arbitrary direction, is substantially obtained.

The memory unit 106 may comprise storage media, such as a ROM, a RAM, a flash memory, which is the nonvolatile memory that can be written and erased electrically, or an HDD (Hard Disc Drive). The memory unit 106 stores X-ray images output from the X-ray image generation unit 102 or the image-processing unit 103.

The display unit 107 comprises a liquid crystal display, etc. and displays X-ray images output from the X-ray image generation unit 102 or the image-processing unit 103. The display unit 107 also displays an operation screen, etc. for operating the X-ray imaging apparatus 1.

The input unit 108 comprises, for example, a touch-panel display and a mechanical button and receives input from the user of the X-ray imaging apparatus 1 via the input unit 108. The input unit 108 outputs various direction signals for, for example, an X-ray beam irradiation direction, a collimator move direction, a C arm driving direction, and a tabletop driving direction, to the imaging control unit 101, according to an input.

The X-ray control unit 201 applies a high voltage for irradiating X-rays to the X-ray tube 301 in response to the X-ray beam irradiation signal output from the imaging control unit 101. Application of the high voltage is performed along with the X-ray parameter specified by the X-ray beam irradiation signal, and an X-ray parameter specifies parameters, such as tube voltage, pipe current, and X-ray pulse width. The X-ray control unit 201 also applies an electric signal for driving a motor attached to the collimator 300 in response to the collimator moving signal output from the imaging control unit 101. This electric signal is applied according to the irradiation field parameter specified by the collimator-moving signal, and the irradiation field parameter specifies the position of the collimator 300 at the time of imaging an X-ray image.

The X-ray tube 301 irradiates X-rays towards the X-ray detector 302, which is arranged to oppose the X-ray tube 301 in response to the high voltage applied from the X-ray control unit 201. The irradiated X-rays are blocked by the collimator 300 to narrow the irradiation field. The X-rays passed through the opening of the collimator 300 penetrate the object P and are irradiated onto the X-ray detector 302. The penetration of the X-rays through the object P causes their intensity changes.

The X-ray detector 302 detects X-rays irradiated from the X-ray tube 301 and outputs an X-ray detection signal to the X-ray image generation unit 102. The X-ray detector 302 comprises a so-called plane detector, in which X-ray detection elements for detecting the incident X-rays and outputting an electric signal according to the amount of detection are arranged in two-dimensional arrays. In this embodiment, the X-ray detector 302 using the plane detector is described as the structure of the X-ray imaging apparatus 1, but the invention is not limited to this. The X-ray detector 302 may be various apparatuses, such as an image intensifier and a television camera.

A collimator 300 is a board containing substances (e.g., lead and tungsten), which block X-rays. The collimator 300 is arranged to cover a direction of radiation from the X-ray tube 301 to block a part of the irradiated X-rays. A motor (not illustrated) is attached to the collimator 300 and the motor moves the position of the collimator 300 according to a collimator moving signal output from the X-ray control unit 201.

A C arm driving unit 202 comprises a plurality of rotary motors and is configured to move the collimator 300, the X-ray tube 301 and the X-ray detector 302, which are attached to the C arm 400, and the C arm 400. The C arm driving units 202 comprises a rotary motor for rotating the C arm 400 around the object P by setting the y-axis in FIG. 1 as a rotation center, a rotary motor for rotating the C arm 400 to the object P by setting the z-axis as a rotation center, a rotary motor for rotating the collimator 300, the X-ray tube 301 and the X-ray detector 302 to the object P by setting the x-axis in FIG. 1 as a rotation center, and a rotary motor for rotating the C arm 400 to the floor by setting the x-axis in FIG. 1 as a rotation center. The C arm driving unit 202 drives each motor according to a C arm driving direction signal output from the imaging control unit 101 and moves the C arm, the collimator 300, the X-ray tube 301 and the X-ray detector 302, which are attached to the C arm.

The C arm 400 is a C shaped component attached to the C arm-driving unit. The collimator 300 and the X-ray tube 301 are attached to one end of the C arm 400, and the X-ray detector 302 is attached to another end of the C arm 400 to face the X-ray tube 301.

The tabletop 500 is a plate shaped component, which may carry and lay the object P. The tabletop 500 is attached to tabletop driving unit 203. The tabletop driving unit 203 (mentioned below) moves the tabletop 500 along a longitudinal direction (the z axis direction in FIG. 1) of the tabletop 500.

The tabletop driving unit 203 comprises a motor (not illustrated), etc., and moves the tabletop 500. The tabletop driving unit 203, for example, has a belt connected to the motor, which is attached to the tabletop 500. The tabletop driving unit 203 rotates the motor according to the tabletop driving direction signal output from the imaging control unit 101, and moves the tabletop 500 along the longitudinal direction (the z axis direction in FIG. 1) of the tabletop 500.

Figure 2:
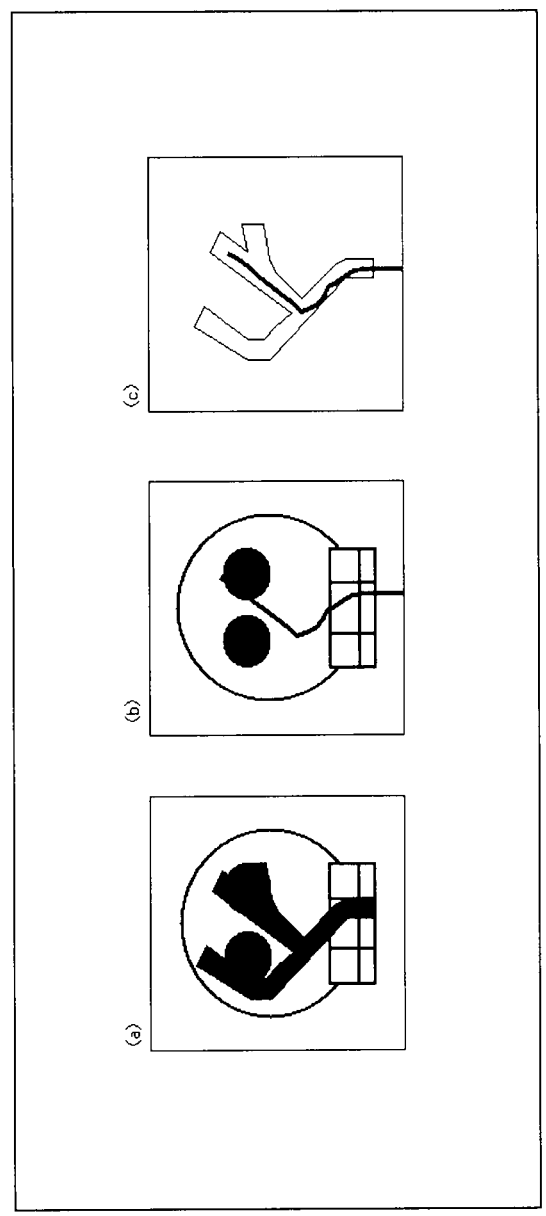
FIG. 2 is a view showing an X-ray image according to the first embodiment of the present invention.

FIG. 2 is a view showing an exemplary X-ray image captured or generated by the X-ray imaging apparatus 1.

FIG. 2 (*a*) shows an X-ray image (hereafter indicated as an "contrast-enhanced image") captured and obtained at the diagnostic part of the object in manipulation where contrast agents are injected.

The X-rays irradiated from X-ray tube 301 change the intensity greatly when penetrating the contrast agents, which exists in the blood vessel of an object, and are incident onto the X-ray detector 302.

Therefore, in addition to a background, such as a bone of an object, the blood vessel of the object will be reflected and crowded in the contrast-enhanced image, which is output from the X-ray image generation unit 102.

FIG. 2 (*b*) shows an X-ray image (hereafter referred to as a "live image") obtained by capturing an image in a state where various insertion instruments for inspection or medical treatment, such as a catheter, a coil, a balloon or a guide wire (hereafter referred as a "device") is inserted into the diagnostic part of the object during manipulation. The X-rays irradiated from X-ray tube 301 penetrates the device to changes the intensity of the X-rays greatly and are incident onto the X-ray detector 302. The live image output from the X-ray image generation unit 102 includes the device, which is inserted into the object, in addition to a background, such as a bone of the object.

FIG. 2 (*c*) shows an X-ray image (hereafter referred as a "subtraction image") obtained by performing the subtraction processing for a contrast-enhanced image and a live image. When the image-processing unit 102 performs the subtraction processing using the contrast-enhanced image and the live image, a background, such as a bone, which appears in common with the image with the contrast medium and the live image disappear, and the blood vessel captured in the image with the contrast medium and the device captured in the live image appear. Therefore, a blood vessel and the device inserted into the blood vessel appear in the subtraction image output from the image-processing unit 103. The user of the X-ray imaging apparatus 1 performs manipulation based on the subtraction image displayed as a moving image by generating and displaying the subtraction image on a real time basis, and performs manipulation while checking the physical relationship of the blood vessel and the device.

Figure 3:
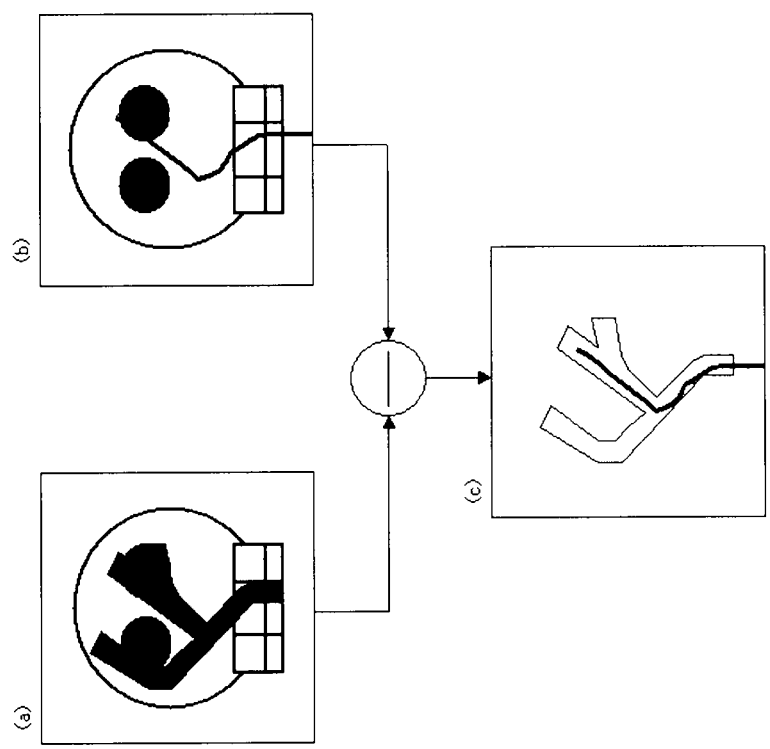
FIG. 3 is a view showing generation processing of a subtraction image according to the first embodiment of the present invention.

FIG. 3 is a view showing generation processing of a subtraction image according to the first embodiment of the present invention. The generation processing of the subtraction image performed by the image-processing unit 103 will be described below. In FIG. 3, explanation of the pixel shift processing (described below) is omitted for simplicity.

The X-ray imaging apparatus 1 performs capturing the contrast-enhanced image as a preceding stage of the subtraction image generation. In order to capture the contrast-enhanced image (a), the imaging control unit 101 drives the C arm 40 and the tabletop 500 and matches the imaging position of the X-ray tube 301 and the X-ray detector 302 with the diagnostic part of the object P. The imaging control unit 101 captures an X-ray image of the object, into which a contrast medium is injected in a case where the imaging position matches with the diagnostic part. The X-ray image generation unit 102 outputs the captured X-ray image (i.e., a contrast-enhanced image (a)) to the memory unit 106.

When capturing of the contrast-enhanced image (a) is finished and insertion of the device into the object is started, the X-ray imaging apparatus 1 captures a live image (b) of the object in manipulation. Capturing the live image (b) is performed at the same imaging position as that of the contrast-enhanced image (a). The imaging control unit 101 captures an X-ray image of the object P in which a device, such as a catheter, is inserted. The X-ray image generation unit 102 outputs the captured X-ray image (i.e., the live image (b)) to the memory unit 106. Capturing the live image (b) is performed based on a direction from a user via the input unit 108 on a real time basis. When capturing the live image (b), which is a moving image on a real time basis, the X-ray tube 301 keeps irradiating X-rays onto the object P, and the X-ray detector 302 outputs the X-ray detection signal to the X-ray image generation unit 102 one after another. Therefore, the live image (b), which is output from the X-ray image 102, changes every moment according to the movement of the object itself due to the movement of the device inserted into the object or the motion of the object.

Next, the image-processing unit 103 performs the subtraction processing for the captured contrast-enhanced image (a) and the captured live image (b), generates a subtraction image (c), and outputs the subtraction image (c) to the display unit 107. A background, such as a bone, which appears in common with the contrast-enhanced image (a) and the live image (b), are deleted by the subtraction processing, and the blood vessel and the device, which are the difference of the contrast-enhanced image (a) and the live image (b), are captured in the subtraction image (c), overlapping with each other.

The image-processing unit 103 performs the subtraction processing using the contrast-enhanced image (a) captured in advance for the live image (b), which changes every moment. Therefore, the generated subtraction image (c) changes every moment according to the change of the live image (b). The user of the X-ray imaging apparatus 1 may confirm the subtraction image displayed on the display unit 107 by sight and perform a manipulation while checking the position of the device in a blood vessel.

By the above processing, the image-processing unit 103 generates the subtraction image (c). When the object P moves by motion etc., deletion of the background and an overlapped display at the time of the subtraction processing are not performed correctly, and a motion artifact appears on the subtraction image (c).

Figure 4:
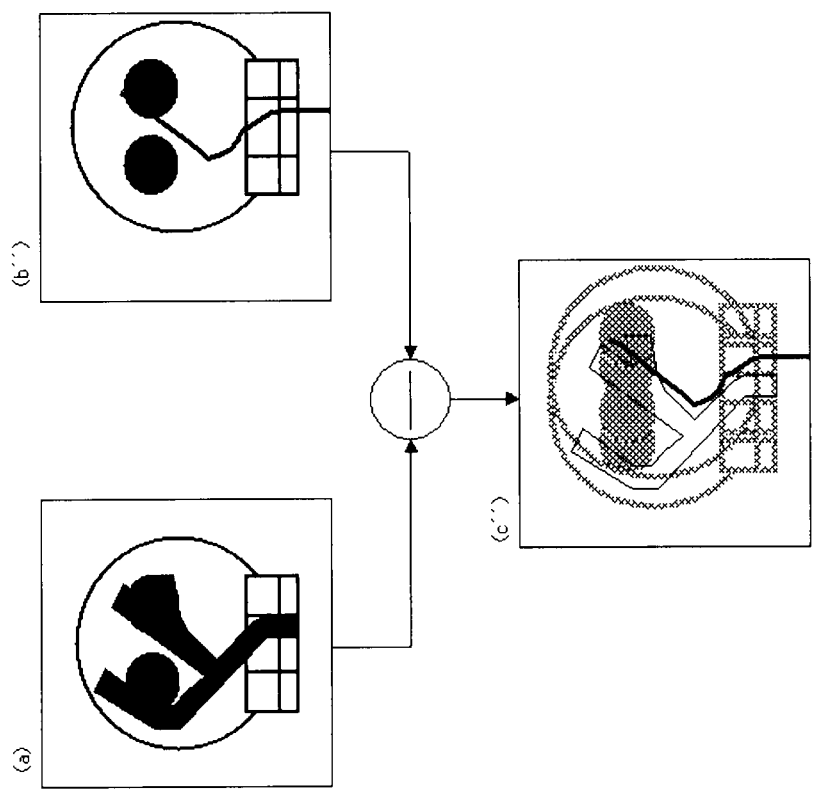
FIG. 4 is a view showing a motion artifact appeared in the subtraction image according to the first embodiment of the present invention.

FIG. 4 is a view showing generation of the subtraction image (c") to the object P that moves during capturing the live image without performing pixel shift processing for reducing the motion artifact control (mentioned below).

When the object P moves during capturing the live image, the X-ray image generation unit 102 outputs the live image (b"), in which the background moved to a different position from the position of the background in the contrast-enhanced image (a). The image-processing unit 103 performs the subtraction processing to the contrast-enhanced image (a) and the live image (b"). Since the difference of both of the X-ray images is mapped by performing the subtraction processing, on the subtraction image (c"), the background before moving, which is captured in the contrast-enhanced image (a), and those after moving, which is captured in the live image (b"), are overlapped and displayed. Further, on the subtraction image (c"), a blood vessel is displayed in the position corresponding to the object P before moving. Since the device inserted into the object P is displayed in the position corresponding to the object P after moving, the blood vessel and the device are displayed at a different display position in a subtraction image (c"). Since the user cannot grasp the position of the device in the blood vessel correctly and the overlapped background is displayed as a hindrance to image recognition, it is difficult to perform manipulation using the subtraction image (c") for the user of X-ray imaging apparatus 1.

Then, in the first embodiment, the subtraction image (c') with reduced motion artifacts is generated by performing pixel shift processing for a contrast-enhanced image (a).

Figure 5:
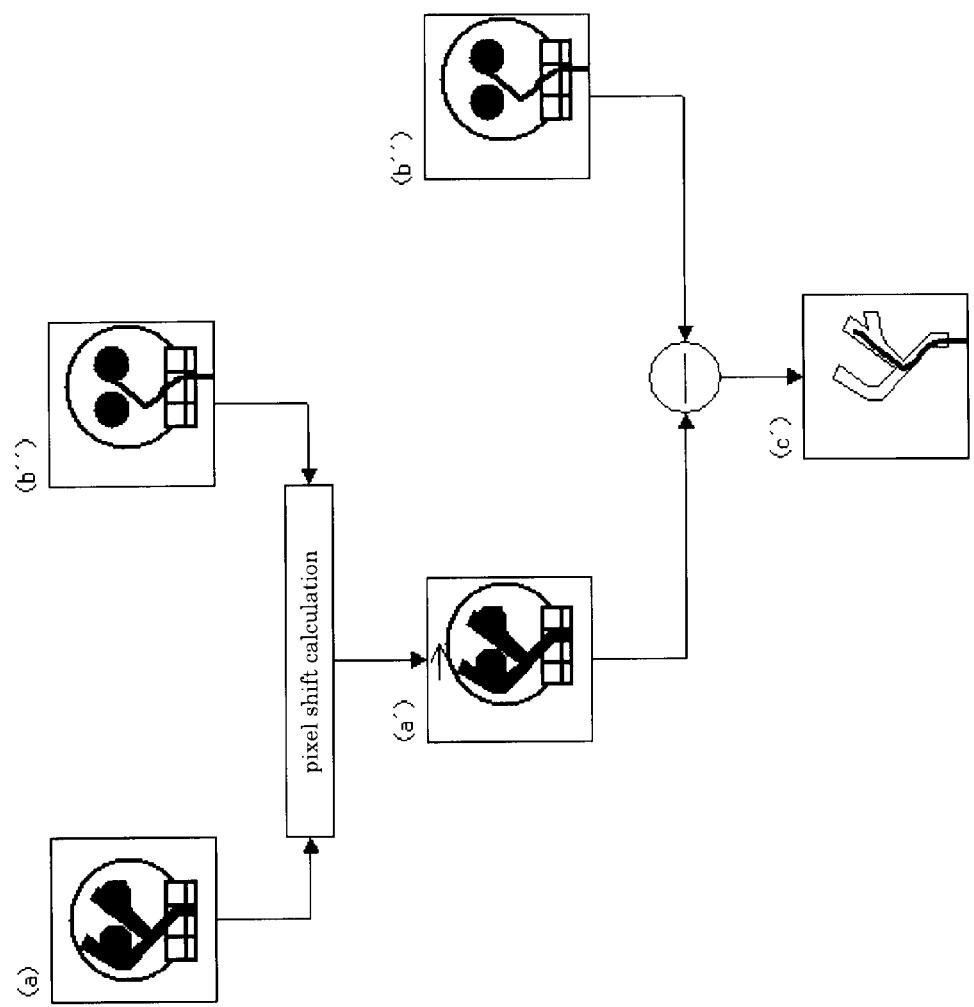
FIG. 5 is a view showing generation processing of the subtraction image using a pixel shift according to the first embodiment of the present invention.

FIG. 5 is a view showing generation of the subtraction image (c') to the object P, which moves during capturing the live image, with pixel shift processing for reducing the motion artifact control (mentioned below). The generation processing of a subtraction image (c') which the image-processing unit 103 performs is described.

When the object P moves during capturing a live image, as stated above, the X-ray image generation unit 102 outputs the live image (b"), in which the background is moved to a different position from those in the contrast-enhanced image (a). First, the image-processing unit 103 calculates a pixel shift amount using the live image (b") and the contrast-enhanced image (a). The image-processing unit 103 substantially calculates the moving direction and the moving distance of the object P on the live image (b") by calculating the pixel shift amount.

Calculation of the pixel shift amount may be realized by the following processing. For example, the square value or the absolute value of the difference between each pixel of the contrast-enhanced image (a) and that of the live image (b") is calculated, and an index value is obtained by adding these values. Next, predetermined amount of pixel shift processing is performed for the contrast-enhanced image (a) and the index value is again calculated between the contrast-enhanced images (a) to which the pixel shift processing of is performed and the live images (b"). This index value is calculated by changing direction and distance of the pixel shift processing to various values, and the direction and distance which has the minimum index value is obtained. The position having the minimum index value may be the position where overlap between the contrast-enhanced image (a) and the live image (b") is maximum. That is, the direction and distance from which the index value is minimum may be the direction and distance where the object moved at the time of capturing the live image (b").

In this embodiment, the direction and distance of the exemplary pixel shift processing is calculated using the above mentioned index value, but the structure of the X-ray imaging apparatus 1 is not limited to this. For example, direction and distance of the exemplary pixel shift processing may be calculated by detecting feature points appeared in the contrast-enhanced image (a) and the live image (b") in common and calculating the positional relationship of these feature points.

When the image-processing unit 103 calculates the direction and distance of the pixel shift processing, the image-processing unit 103 generates the contrast-enhanced image (a'), to which pixel shift processing is performed, based on the calculated direction and distance. Substantially, the contrast-enhanced image (a') may be the image where the background and the blood vessel appeared in the contrast-enhanced image (a') are moved to the positions which overlap with the background appeared in the live image (b").

When the image-processing unit 103 generates the contrast-enhanced image (a'), the subtraction processing is performed for the contrast-enhanced image (a') and the live image (b"), the subtraction image (c') is generated and output to the display unit 107. Since the background and blood vessel in the contrast-enhanced image (a') are moved according to the background of the live image (b"), the background, such as a bone, which appears in the contrast-enhanced image (a') and the live image (b') in common, are deleted. Thus, the blood vessel, which is the difference between the contrast-enhanced image (a') and the live image (b"), and the device are captured in the subtraction image (c'), overlapping with each other.

By the above processing, the image-processing unit 103 generates a subtraction image by pixel shift processing and the subtraction processing. Even when the object P moves during capturing a live image, the subtraction image with reduced motion artifact may be obtained since the image-processing unit 103 calculates the amount of movements and performs pixel shift processing to the contrast-enhanced image according to the amount of movements. Moreover, the burden to the object P due to the injection of contrast agents and the irradiation of X-rays are reduced since it is not necessary to recapture the contrast-enhanced image when the object moves. Further, manipulation time may be shortened since there is no discontinuation of manipulation due to re-capturing the contrast-enhanced image.

In generation processing of the subtraction image explained in FIG. 5, calculation processing of a pixel shift amount using a contrast-enhanced image and a live image is performed. The generation processing of a subtraction image shown in FIG. 5 for all the live images output from the X-ray image generation unit 102, may be a hindrance of real-time generation of a subtraction image because the calculation processing of this pixel shift amount may increase calculation load.

In order to avoid such a situation, in each embodiment, generation processing of a subtraction image without pixel shift processing shown in FIG. 3 is performed, and generation processing of the subtraction image using pixel shift processing as shown in FIG. 5 is performed only when the object moves.

Figure 6:
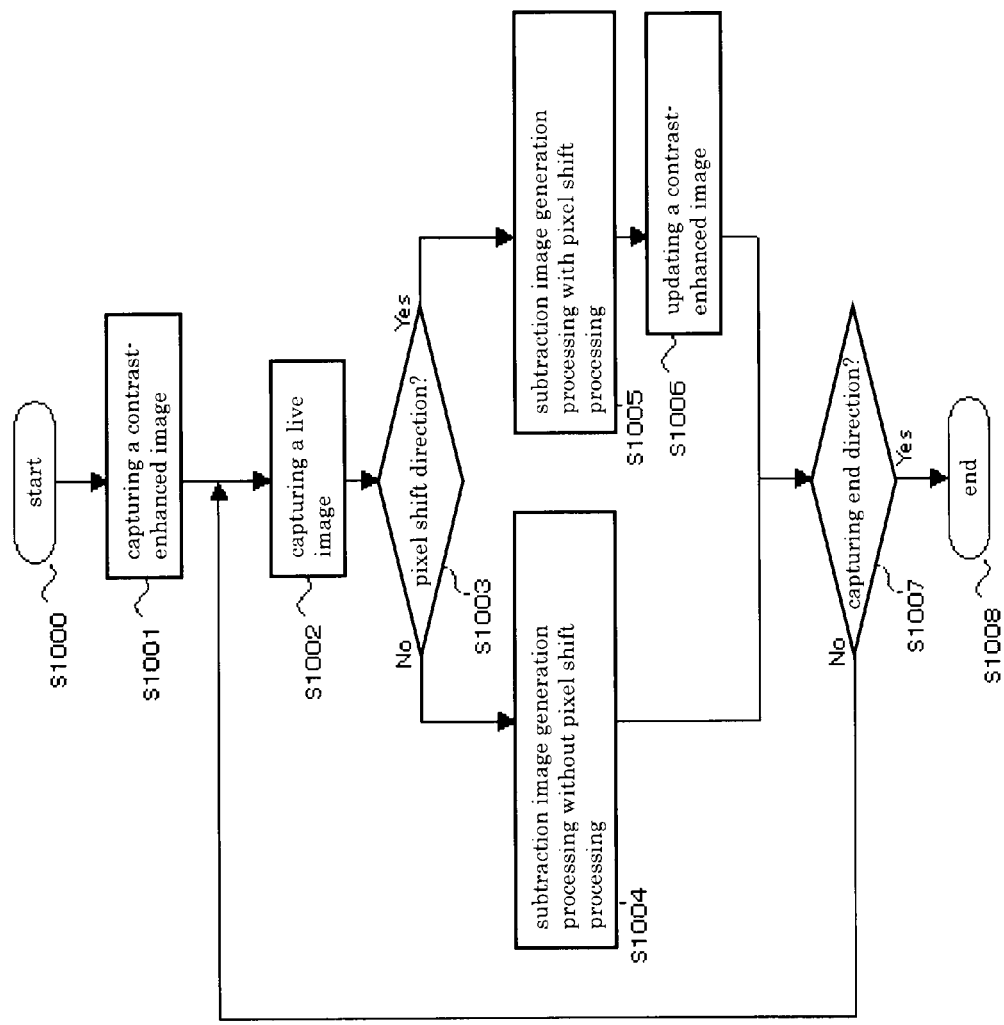
FIG. 6 is a flowchart showing generation processing of subtraction processing according to the first embodiment of the present invention.

FIG. 6 is a flowchart showing generation processing of subtraction processing with judgment of pixel shift processing. The processing flow is stated below with reference to FIG. 6.

When the X-ray imaging apparatus 1 starts generation processing of a subtraction image first (Step 1000), the X-ray image generation unit 102 performs capturing a contrast-enhanced image as a preceding stage of subtraction image generation (Step 1001). After the X-ray image generation unit 102 finishes capturing a contrast-enhanced image, the X-ray image generation unit 102 captures a live image continuously (Step 1002). Next, the control unit 100 judges whether the pixel shift direction is input from the input unit 108 (Step 1003). The pixel shift direction is performed by the user of X-ray imaging apparatus 1 using the input unit 108. For example, these directions are performed when a user confirms visual recognition by sight or a user visual confirms a motion artifact from a subtraction image by sight.

When the control unit 100 judges that there is no input of pixel shift direction ("No" of Step 1003), the image-processing unit 103 performs subtraction image generation processing without the pixel shift processing shown in FIG. 3 using a contrast-enhanced image and a live image (Step 1004). When the control unit 100 judges that pixel shift direction is input ("Yes" of Step 1003), the image-processing unit 103 performs subtraction image generation processing with the pixel shift processing shown in FIG. 5 using a contrast-enhanced image and a live image (Step 1005). The image-processing unit 103 updates a contrast-enhanced image to the image with pixel shift as well as generating a subtraction image (Step 1006). That is, in the processing after Step 1006, the contrast-enhanced image for which the pixel shift is performed when a subtraction image is generated.

When processing of Step 1004 or Step 1006 finishes, the control unit 100 judges whether the capturing end direction is input from the input unit 108 (Step 1007). When the control unit 100 judges that capturing end direction is not input ("No" of Step 1007), the control unit 100 returns to Step 1002 where the X-ray image generation unit 102 captures a live image and continues processing. When the control unit 100 judges that the capturing end direction is input ("Yes" of Step 1007), the control unit 100 finishes processing.

By the above processing, the control unit 100 uses properly the subtraction image generation processing with pixel shift processing and the subtraction image generation processing without pixel shift processing. By performing subtraction image generation processing with pixel shift processing only when the direction is input from the input unit 108, the calculation load to the control unit 100 is reduced.

The judgment in Step 1003 is described to be performed based on whether pixel shift direction is input from the input unit 108. However, processing of this embodiment is not limited to this. For example, a judgment of shifting to processing of Step 1005 may be entered according to input of the control signal, which stops capturing a live image, from the input unit 108 in place of pixel shift direction. Calculation processing of a pixel shift amount may be performed with the stop of live image imaging, and therefore the calculation processing of a pixel shift amount with a small processing load of capturing live image may be performed. Time of continuous processing of Step 1004 without processing of Step 1005 may be measured, and a judgment of shifting to processing of Step 1005 may be entered according to excess of predetermined time (for example, 30 seconds)

The judgment of pixel shift processing described with reference to FIG. 6 may be applied to each embodiment (mentioned below) in a similar way. In that case, the contrast-enhanced image updated in Step 1006 may be replaced with, for example, a mask image, a blood vessel image and a roadmap image, which are described below.

Second Embodiment

Next, the second embodiment of X-ray imaging apparatus 1 is explained.

In the second embodiment, similar elements of the X-ray imaging apparatus 1 are designated by the same reference numeral, and its explanation is omitted. In this second embodiment, generation processing of a different subtraction image differs from the first embodiment as described below.

Figure 7:
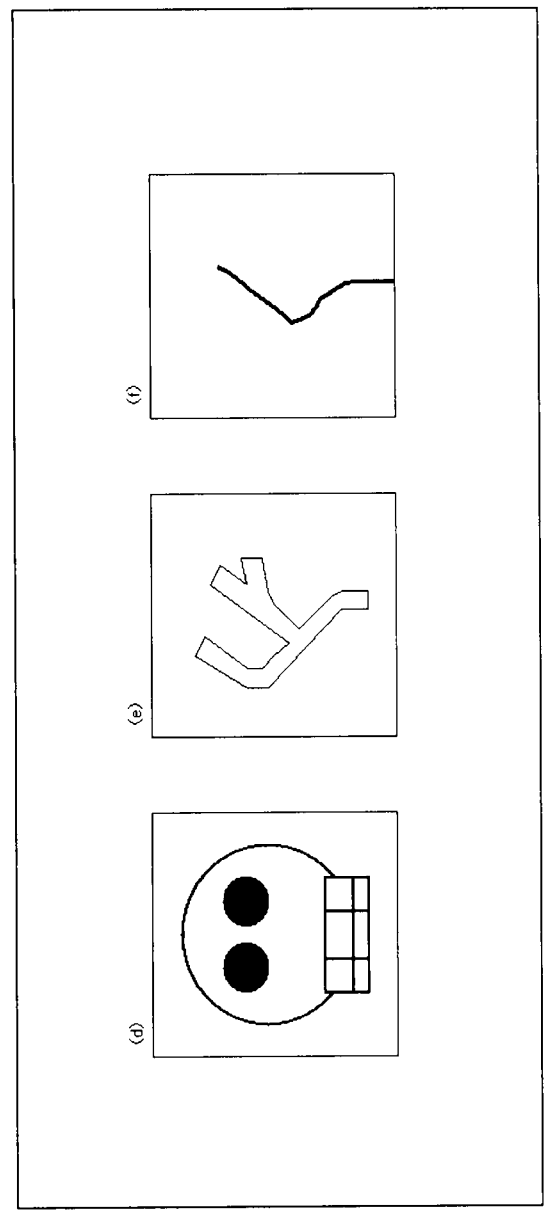
FIG. 7 is a view showing an X-ray image according to the second embodiment of the present invention.

FIG. 7 is a view showing an X-ray image, which is generated and captured by X-ray imaging apparatus 1 captures or generates.

FIG. 7 (d) shows a non-contrast X-ray image (hereinafter, referred to as a "mask image") which is captured in a case where contrast agents are not injected to the diagnostic part of the object before or contrast agents has passed. This mask image includes a background, such as a bone of the object.

FIG. 7 (e) shows an X-ray image (hereinafter, referred to as a "blood vessel image") which is obtained by performing subtraction processing between a contrast-enhanced image and a mask image. When the image-processing unit 102 performs the subtraction processing using the contrast-enhanced image and the mask image, a background, such as a bone, which are captured in common with the contrast-enhanced image and the mask image, disappear, and the blood vessel which is only captured in the contrast-enhanced image appears. Therefore, only the blood vessel in the contrast-enhanced image is extracted to be captured in the blood vessel image output from the image-processing unit 103.

FIG. 7 (f) shows an X-ray image (hereafter referred to as a "wire image") which is obtained by performing the subtraction processing between a live image and a mask image. When the image-processing unit 102 performs the subtraction processing using the live image and the mask image, a background, such as a bone, which is captured in common with the live image and the mask image, disappears, and the device, which is captured only in the live image, appears. Therefore, only the device in a live image is extracted to be captured in the wire image which is output from the image-processing unit 103.

Figure 8:
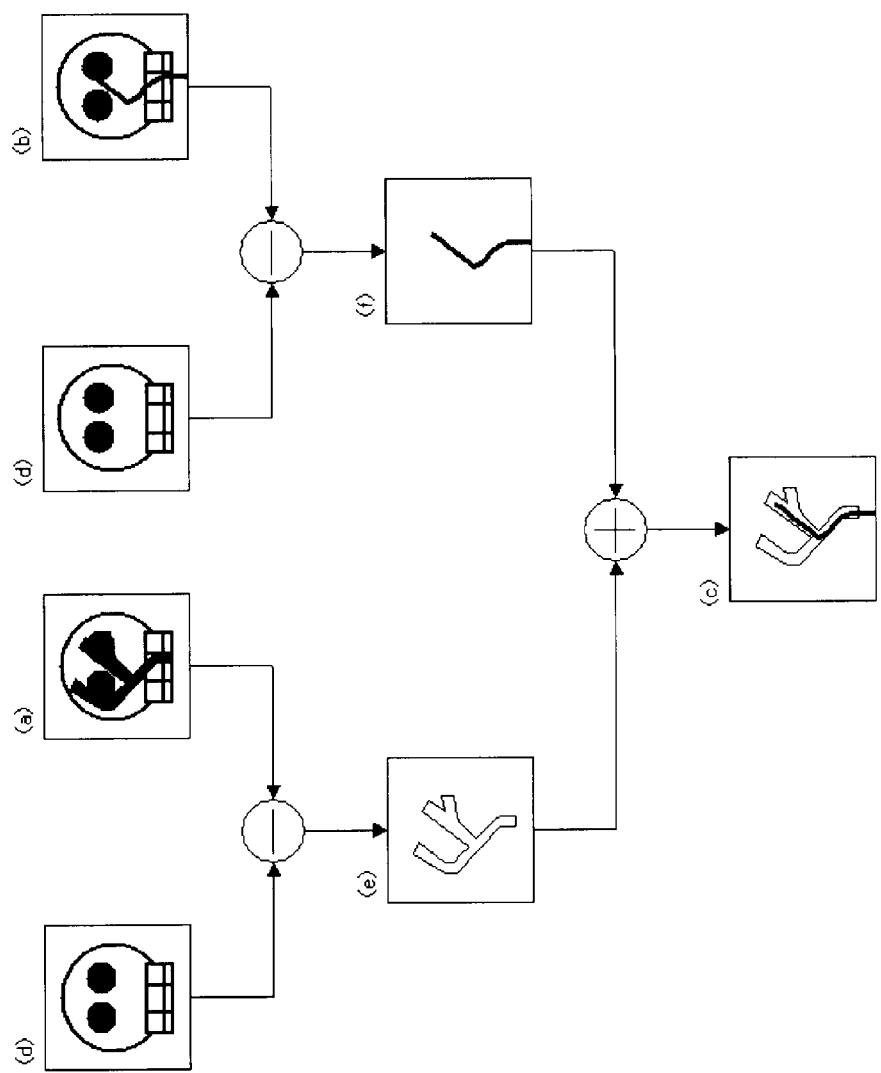
FIG. 8 is a view showing generation processing of a subtraction image according to the second embodiment of the present invention.

FIG. 8 is a view showing generation processing of a subtraction image according to the second embodiment of the present invention. Hereafter, the generation processing of a subtraction image performed by the image-processing unit 103 performs is described. In FIG. 8, explanation of the pixel shift processing (mentioned below) is omitted for simplicity.

The X-ray imaging apparatus 1 performs capturing a mask image (d) and a contrast-enhanced image (a). In order to capture the mask image (d), the imaging control unit 101 drives the C arm 400 and the tabletop 500, and matches the imaging position by the X-ray tube 301 and the X-ray detector 302 with the diagnostic part of the object. After matching the imaging position with the diagnostic part, the imaging control unit 101 captures an X-ray image of the object into which contrast agents is not injected. The X-ray image generation unit 102 outputs the captured X-ray image (i.e., a mask image (d)) to the memory unit 106.

When the X-ray image generation unit 102 outputs the mask image (d) to the memory unit 106, the X-ray imaging apparatus 1 captures a contrast-enhanced image (a). The imaging position of the contrast-enhanced image (a) is similar to that of a mask image (d). The imaging control unit 101 captures an X-ray image of the object into which contrast agents are injected when the imaging position matches with that of the mask image (d). The X-ray image generation unit 102 outputs the captured X-ray image (i.e., a contrast-enhanced image (a)) to the memory unit 106.

When the mask image (d) and the contrast-enhanced image (a) are output to the memory unit 106, the image-processing unit 103 performs subtraction processing to the mask image (d) and the contrast-enhanced image (a) to generate a blood vessel image (e) and outputs the blood vessel image (e) to the memory unit 106. By the subtraction processing, a background, such as a bone, which is captured in common with the mask image (d) and the contrast-enhanced image (a), is deleted, and blood vessel image (e) shows the blood vessel which is captured on in the contrast-enhanced image (a).

When generation of the blood vessel image (e) finishes and manipulation to the object starts, the X-ray imaging apparatus 1 captures a live image (b) of the object in manipulation. Capturing a live image (b) is performed at the same imaging position as in the contrast-enhanced image (a) and the mask image (d). The imaging control unit 101 captures a live image (b), which is a moving image on a real time basis, of the object P into which the device is inserted and outputs the live image (b) to the memory unit 106 one after another. Therefore, the live image (b) changes every moment according to the movement of the object itself due to, for example, the movement of the device inserted into the object or the motion of the object.

Next, the image-processing unit 103 performs the subtraction processing to the captured mask image (d) and the captured live image (b) to generate a wire image (f), and outputs the wire image (f) to the memory unit 106. A background, such as a bone, which is captured in common with the mask image (d) and the live image (b) is deleted by the subtraction processing, and the device, which is only captured in the live image (b), is displayed on the wire image (f). Moreover, the wire image (f) changes according to according to the live image (b), which changes every moment according to the positional relationship between the object and the device.

When the image-processing unit 103 generates the wire image (f), the image-processing unit 103 combines a wire image (f) and a blood vessel image (e) to generate a subtraction image (c). More specifically, the image-processing unit 103 adds the pixel value mapped in a coordinate of the wire image (f) and that mapped in the same coordinate of the blood vessel image (e), and maps the added values to the same coordinate of the subtraction image (c). The subtraction image (c) is generated by repeating additions and mappings of these pixel values for each coordinates of the subtraction image (c). By this additions, the subtraction image (c) shows a combination of the device captured in the wire image (f) and the blood vessel captured in the blood vessel image (e). Since the wire image (f) changes according to the change of the live image (b) as mentioned above, the subtraction image (c) changes according to the live image (b) which changes every moment according to the positional relationship between the object and the device.

When the image-processing unit 103 generates the subtraction image (c), the image-processing unit 103 outputs the subtraction image (c) on the display unit 107. The user of the X-ray imaging apparatus 1 may confirm the subtraction image (c) displayed on the display unit 107 by sight and perform a manipulation, checking the position of the device in a blood vessel. Unlike the generation of the subtraction image stated in the first embodiment, in the second embodiment, the subtraction image (c) is generated by combining the blood vessel image (e) which has only the blood vessel and the wire image (f) which has only the device. By performing weighting of the pixel values of the blood vessel image (e) and the wire image (f) according to the direction signals input from, for example, the input unit 108, display concentration of the blood vessel and the device which appear on the subtraction image (c) may be changed to suitable concentration.

By the above processing, the image-processing unit 103 generates the subtraction image (c). However, a motion artifact appears in the wire image (f) and the subtraction image (c) when the object moves by motion, etc.

Figure 9:
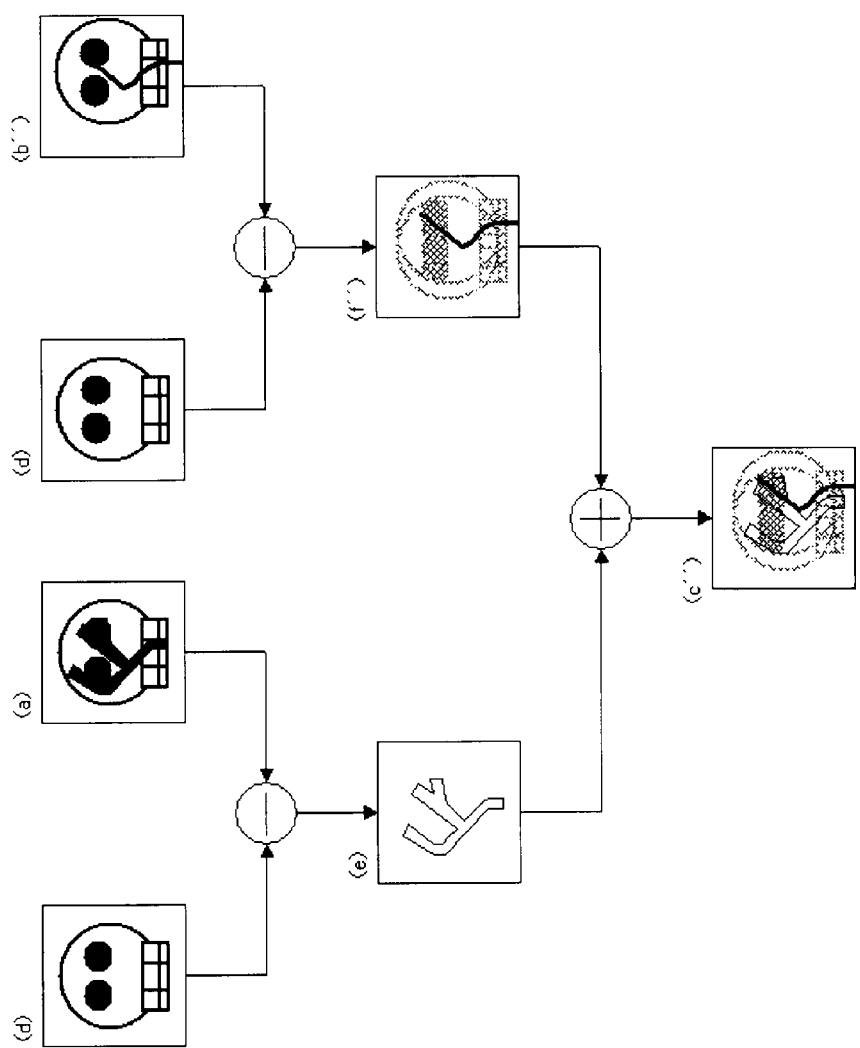
FIG. 9 is a view showing a motion artifact appeared in the subtraction image according to the second embodiment of the present invention.

FIG. 9 is a view showing generation of a wire image (f") and a subtraction image (c") without performing pixel shift processing for reducing the motion artifact control (mentioned below) for the object, which moves during capturing a live image. When the object P moves during capturing a live image, the X-ray image generation unit 102 outputs a live image (b") which has a background moved to a different position from that of the background in a mask image (d). The image-processing unit 103 performs subtraction processing to the mask image (d) and the live image (b"). Since difference of both the X-ray images is mapped by performing the subtraction processing, on the wire image (f"), the background before moving which is captured in the mask image (d), the background after moving which is captured in the live image (b") and the devices which is inserted into the object are displayed to overlap each other.

Further, the image-processing unit 103 generates the subtraction image (c") based on the wire image (f") and a blood vessel image (e). In the subtraction image (c"), a background and a blood vessel located at the position corresponding to that of the object before moving and the background and a devices located at the position corresponding to that of the object after moving are displayed to overlap each other. Since the background which is displayed to overlap each other and a gap between the blood vessel and the device in the subtraction image (c") are hindrance of image recognition by sight, it is difficult for the user of the X-ray imaging apparatus 1 to perform manipulation using the subtraction image (c").

In the second embodiment, the subtraction image (c') with reduced motion artifact is generated by performing pixel shift processing for the mask image (d) and the blood vessel image (e). The generation processing of the subtraction image (c') performed by the image-processing unit 103 is described below with reference to FIG. 10. As a preceding step of the subtraction image (c') generation, generations of the contrast-enhanced image (a), the mask image (d) and the blood vessel image are considered to be finished before the generation processing of the subtraction image (c').

When the object P in manipulation moves during capturing the live image, as mentioned above, the X-ray image generation unit 102 outputs the live image (b") in which the background moves to a different position from that of the background in the mask image (d). The image-processing unit 103 calculates a pixel shift amount using the live image (b") and the mask image (d). By calculating the pixel shift amount, the image-processing unit 103 substantially calculates the direction and distance to which the background moves in the live image (b"). The calculation method of the pixel shift amount is similar to that of the first embodiment.

The image-processing unit 103 generates the mask image (d') to which pixel shift processing based on the calculated direction and distance when the image-processing unit 103 calculates the direction and distance of the pixel shift processing. The mask image (d') is substantially the image which moves according to the movement of the object P.

When the image-processing unit 103 generates the mask image (d'), the image-processing unit 103 generates a wire image (f') which is generated by the subtraction processing between the mask image (d') and the live image (b"), and outputs the wire image (f') to the memory unit 106. Since the background in the mask image (d') moves according to the live image (b"), the background captured in common with the mask image (d') and the live image (b") is deleted, and the wire image (f') which shows the device captured only in the live image (b") is obtained.

While generating the wire image (f'), the image-processing unit 103 performs pixel shift processing for the blood vessel image (e) and generates a blood vessel image (e'). At this time, the direction and distance of the pixel shift processing performed for the blood vessel image (e) are similar to those of the pixel shift processing performed at the time of generating the mask image (d'). Therefore, the blood vessel image (e) is substantially the blood vessel image (e') which is moved according to movement of the object P.

When the image-processing unit 103 generates the wire image (f') and the blood vessel image (e'), the image-processing unit 103 combines both the X-ray images and generates a subtraction image (c'). Although the wire image (f') is moved in the image according to the movement of the object P, the blood vessel image (e') is also moved according to the movement of the object P. Therefore, the subtraction image (c') in which the device and the blood vessel overlap at the correct position is obtained by combining the wire image (f') and the blood vessel image (e').

By the above processing, the image-processing unit 103 generates a subtraction image by pixel shift processing and subtraction processing. The subtraction image with small motion artifact may be generated in a similar way as the first embodiment without performing re-capturing a mask image.

As a result, the burden to the object due to the injection of contrast agents or the X-ray irradiation may be reduced, and manipulation time may be shortened. Moreover, since the pixel shift processing of the mask image and the pixel shift processing of the blood vessel image are performed based on the calculated pixel shift amount even when the blood vessel image and the wire image are generated separately and the subtraction image is generated by combining both the X-ray images, the wire and the blood vessel may be displayed to overlap each other at the right position.

Third Embodiment

Next, the third embodiment of the X-ray imaging apparatus 1 is explained. In the third embodiment, since the structure of the X-ray imaging apparatus 1 and the flow of the generation processing of the subtraction image is in common with the second embodiment, their explanations are omitted. In the third embodiment, unlike the second embodiment, the control unit 100 performs deleting the contrast-enhanced image (a) and the live image (b) from the memory unit 106, which are not necessary in the generation processing during the progress of the generation processing of the subtraction image. Further, in the third embodiment, unlike the second embodiment, the image-processing unit 103 performs processing of re-generating the live image (b), which is necessary to perform pixel shift processing.

Figure 11:
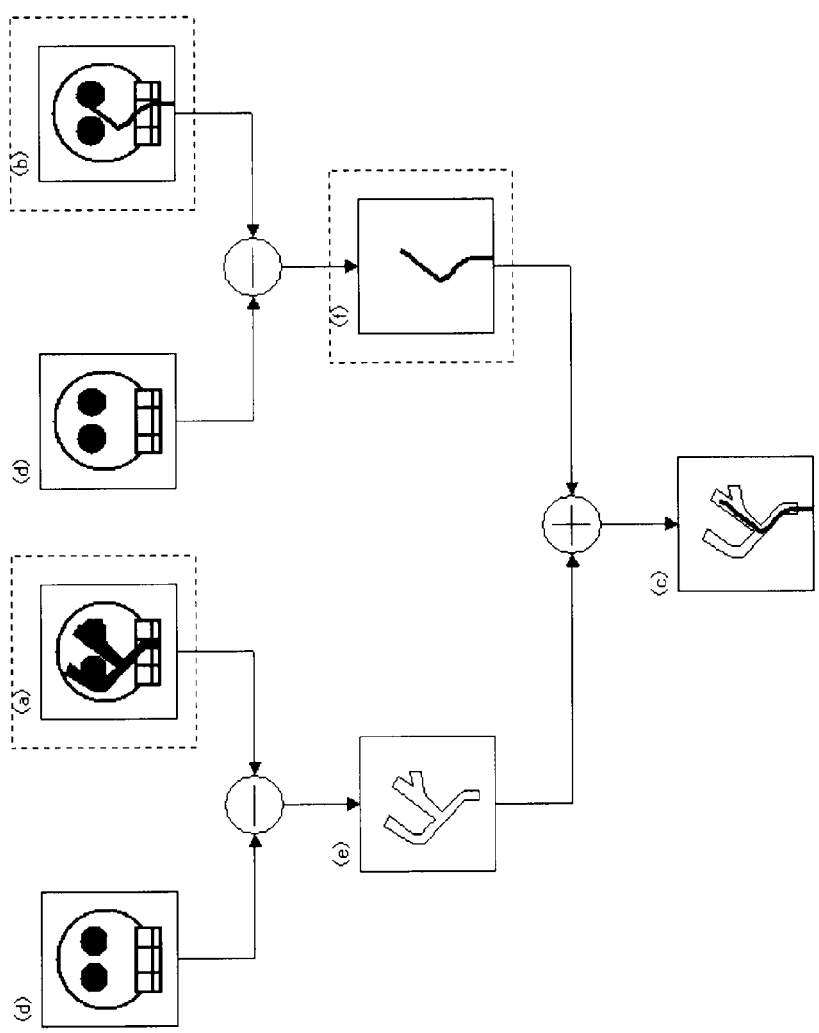
FIG. 11 is a view showing an X-ray image according to the third embodiment of the present invention.

With reference to FIG. 11, processing of deleting the contrast-enhanced image (a) and the live image (b) from the memory unit 106 is explained below. FIG. 11 is a view showing generation processing of the subtraction image according to the third embodiment of the present invention. In FIG. 11, unlike FIG. 8, the images which is temporarily saved in the memory unit 106 and is deleted from the memory unit 106 at the time of the completion of generation of the subtraction image. With reference to FIG. 11, reconstruction processing of a live image is described below.

In the second embodiment as mentioned above, the image-processing unit 103 outputs a contrast-enhanced image (a) and a mask image (d) to the memory unit 106 when the image-processing unit 103 captures the contrast-enhanced image (a) and the mask image (d). The image-processing unit 103 generates a blood vessel image (e) (mentioned below) using the contrast-enhanced image (a) and the mask image (d), which are stored in the memory unit 106. Since generation of a subsequent subtraction image (c) is performed using the live image (b), the mask image (d) and a blood vessel image (e), once the generation of the blood vessel image (e) is performed, the contrast-enhanced image (a) is not used in the generation processing of the subsequent subtraction images. Storing the image data of the contrast-enhanced image (a), which is not used, in the memory unit 106 puts pressure on storage capacity of the memory unit 106 and is inconvenient to next calculation processing or memory processing of the generated X-ray image, the control unit 100 deletes the unused contrast-enhanced image (a) from the memory unit 106, when the control unit 100 generates the blood vessel image (e).

In the second embodiment as mentioned above, the live image (b) is describes as a moving image captured on a real time basis. Therefore, the X-ray image generation unit 102 performs generation of the live image (b) and the wire image (f) and output of the live image (b) and the wire image (f) to the memory unit 106 one after another according to a detection of an X-ray signal continuously performed by the X-ray detector 101. The user of X-ray imaging apparatus 1 may usually perform manipulation, referring to the subtraction image (c) at the time of capturing images, the wire image (f) which is captured in the past and the live image (b) which are generated in the past are unnecessary for performing manipulation. When the control unit 100 finishes generating a subtraction image (c), the control unit 100 deletes the live image (b) and the wire image (f) which are used for generating the subtraction image (c), since storing the live image (b) and the wire image (f) output from the X-ray image generation unit 102 puts pressure on storage capacity of the memory unit 106 and is inconvenient to next calculation processing and memory processing of the generated X-ray images.

Therefore, the contrast-enhanced image (a), the live image (b) and the wire image (f), which are marked by the dotted line in FIG. 11, are temporarily stored in the memory unit 106 and then deleted when finishing generation of the subtraction image (c). When the subtraction image (c) is generated, the mask image (d), the blood vessel image (e) and the subtraction image (c) are stored in the memory unit 106.

Figure 10:
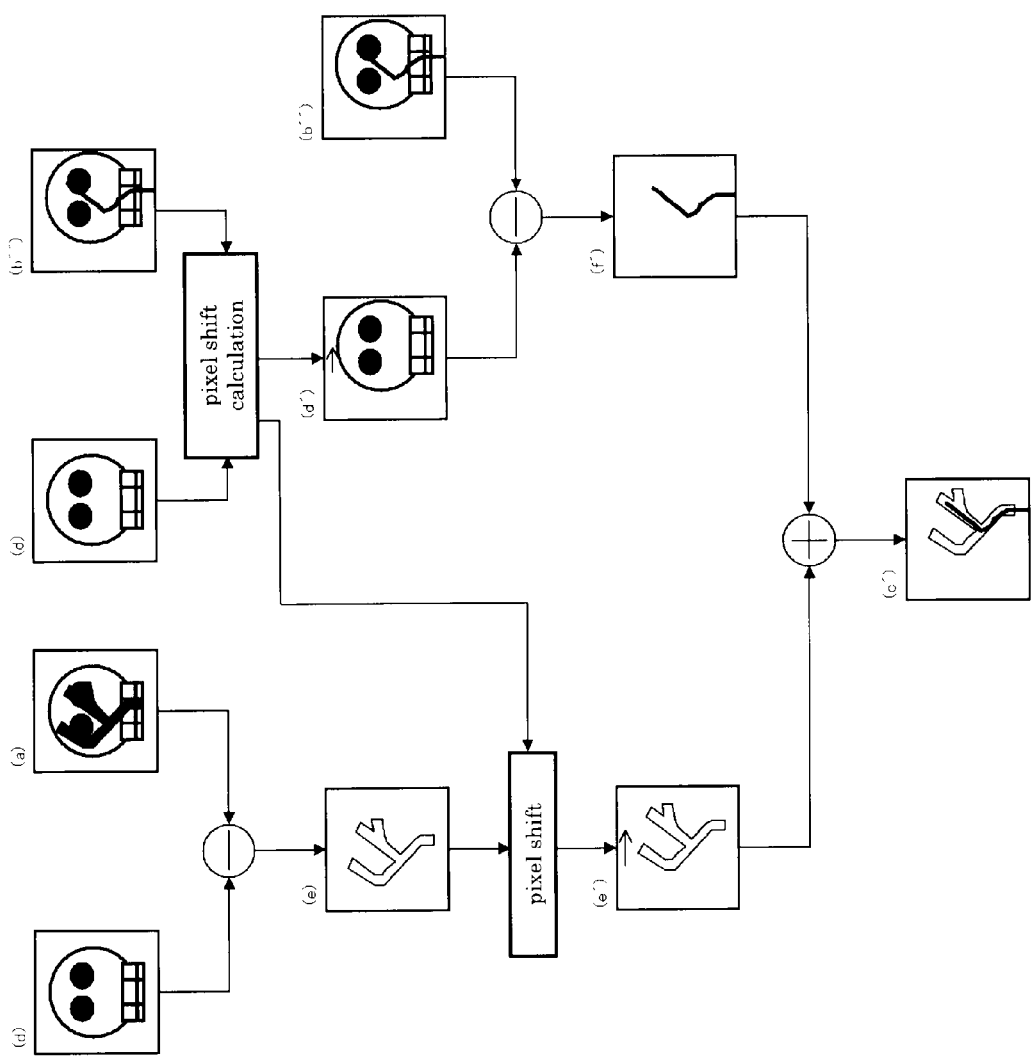
FIG. 10 is a view showing generation processing of the subtraction image using a pixel shift according to the second embodiment of the present invention.
Figure 12:
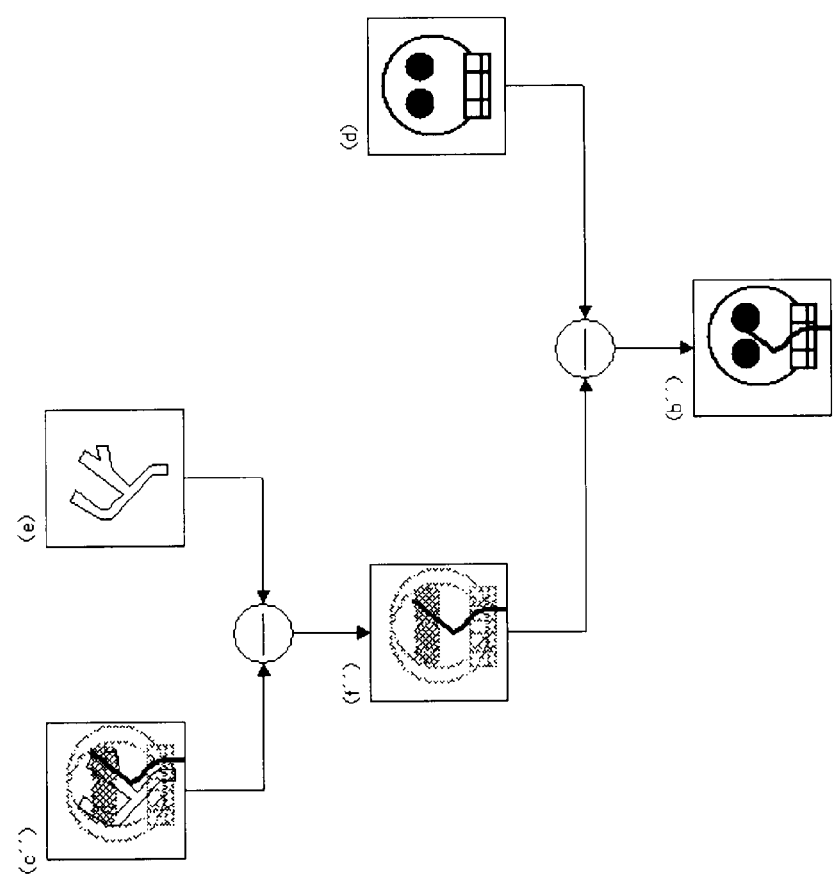
FIG. 12 is a view showing a live image concerning according to the third embodiment of the present invention.

If the object P moves after deleting the contrast-enhanced image (a), the live image (b) and the wire image (f) from the memory unit 106, the image-processing unit 103 performs calculation of the pixel shift amount and pixel shift processing according to the processing described in FIG. 10. However, the image-processing unit 103 cannot proceed the processing since the live image (b"), which is necessary to perform calculation processing of a pixel shift amount, is deleted from the memory unit 106. In the third embodiment, reconstruction processing of the live image (b") is performed as the preceding step of pixel shift processing. With reference to FIG. 12, reconstruction processing of the live image (b") performed by the image-processing unit 103 is described below.

When the object P in manipulation moves while capturing a live image, as described in FIG. 9, the image-processing unit 103 outputs the subtraction image (c") with motion artifact to the memory unit 106.

When the image-processing unit 103 outputs the subtraction image (c") to the memory unit 106, the image-processing unit 103 performs subtraction processing of the subtraction image (c") and the blood vessel image (e) and generates the wire image (f"). The subtraction image (c") includes the background and the blood vessel located at the position corresponding to that of the object P before moving, and the background and the device located at the position corresponding to that of the object P after moving in a state of overlapping each other. When subtraction processing of the subtraction image (c") using the blood vessel image (e) which has the blood vessel located at the position corresponding to the object P before moving is performed, the generated wire image (f") has the background located at the position corresponding to the object P before moving and the background located at the position corresponding to the object P after moving in a state of being overlapped each other. The wire image (f") is substantially re-generated processing of the wire image (f"), which has motion artifact as described in FIG. 9.

When the image-processing unit 103 re-generates the wire image (f"), the image-processing unit 103 performs the subtraction processing of the wire image (f") and the mask image (d) to generate the live image (b"). As mentioned above, the wire image (f") has the background located at the position corresponding to the object P before moving, and the background and device locate at the position corresponding to the object P after moving at the stated of being overlapped each other. When the subtraction processing is performed using the mask image (d) which has the background located at the position corresponding to the object P before moving, the generated live image (b") has the background and the device located at the position corresponding to the object P after moving to be overlapped each other. The live image (b") is substantially the re-generated live image (b") of the object P that moves during manipulation as mentioned in FIG. 9.

When the image-processing unit 103 re-generates the live image (b"), the subtraction image (c') with reduced motion artifact is generated based on the pixel shift processing as described in FIG. 10.

By the above processing, the image-processing unit 103 in the third embodiment performs re-generation processing of the live image deleted from the memory unit 106 as a preceding step for performing pixel shift processing. In addition to the effect of the second embodiment, the subtraction image with reduced motion artifact may be generated, avoiding the pressure of the storage capacity of the memory unit 106 caused by the live images generated one after another as moving images on real time basis.

Fourth Embodiment

Next, the X-ray imaging apparatus 1 according to the fourth embodiment is explained below. In the fourth embodiment, since the structure of the X-ray imaging apparatus 1 is common with the first embodiment, its explanation is omitted. In this embodiment, generation processing which is different from that of each embodiment is explained below.

Figure 13:
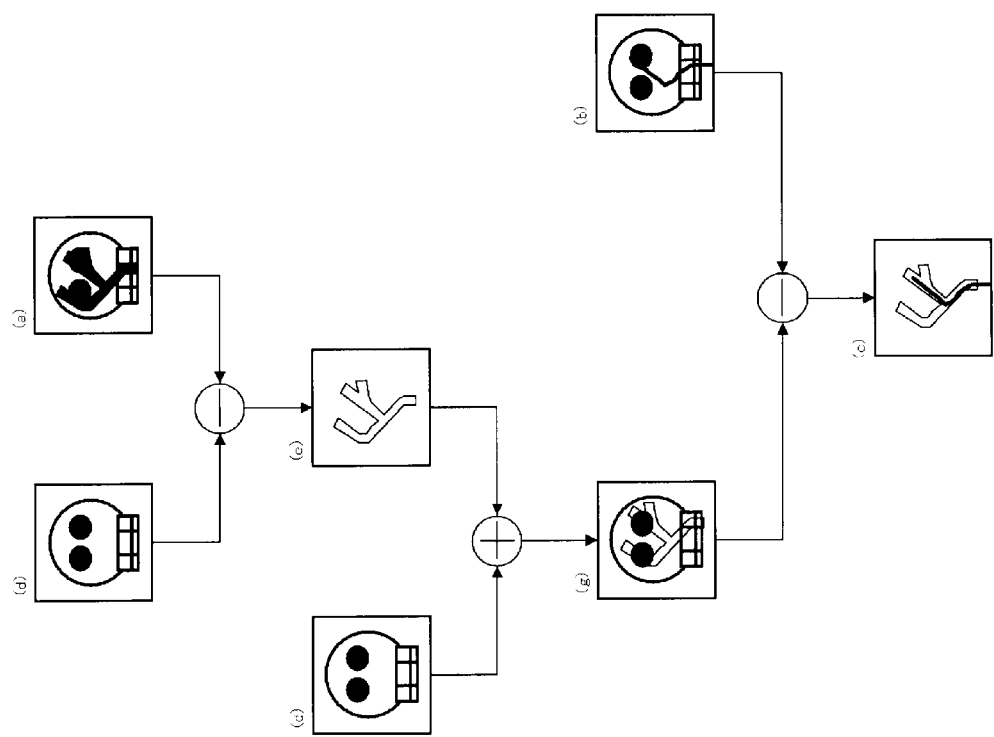
FIG. 13 is a view showing generation processing of a subtraction image according to the fourth embodiment of the present invention.

FIG. 13 is a view showing generation processing of a subtraction image according to the fourth embodiment of the present invention. The generation processing of the subtraction image performed by the image-processing unit 103 is described below. In this embodiment, the pixel shift processing (mentioned below) is omitted for simplicity.

The X-ray imaging apparatus 1 performs capturing a mask image (d) and the contrast-enhanced image (a) as a preceding step the subtraction image generation. In order to capture the mask image (d), the imaging control unit 101 drives the C arm 400 and the tabletop 500, and matches the imaging position of the X-ray tube 301 and the X-ray detector 302 with the diagnostic part of the object P. When the imaging position and the diagnostic part are matched, the imaging control unit 101 captures an X-ray image of the object P into which contrast agents are not injected. The X-ray image generation unit 102 outputs the captured X-ray image (i.e., the mask image (d)) to the memory unit 106.

When the X-ray image generation unit 102 outputs the mask image (d) to the memory unit 106, X-ray imaging apparatus 1 captures a contrast-enhanced image (a) next. The imaging position of the contrast-enhanced image (a) is similar to the mask image (d). When the imaging position are matched with that of the mask image (d), the imaging control unit 101 captures an X-ray image (i.e., the contrast-enhanced image (a)) of the object into which contrast agents are injected. The X-ray image generation unit 102 outputs the captured the X-ray image (i.e., the contrast-enhanced image (a)) to the memory unit 106.

When the mask image (d) and the contrast-enhanced image (a) are output to the memory unit 106, the image-processing unit 103 performs subtraction processing to the mask image (d) and the contrast-enhanced image (a) and generates the blood vessel image (e) to outputs the blood vessel image (e) to the memory unit 106.

By the subtraction processing, a background, such as a bone, which is captured in common with the blood vessel image (e) and the contrast-enhanced image (a) is deleted, and the blood vessel image (e) includes a blood vessel, which is only captured in the contrast-enhanced image (a).

When the X-ray image generation unit 102 generates the blood vessel image (e), the image-processing unit 103 generates the X-ray image (hereafter, referred to as a "roadmap image (g)") which is generated by adding the mask image (d) and the blood vessel image (e). The image-processing unit 103 performs weighting processing for each pixel value mapped in the blood vessel image (e) based on the input from the input unit 108 changes the concentration on the image of the blood vessel image (e). In this weighting processing, for example, if the user of the X-ray image generation unit 102 wants to display the blood vessel appeared in the subtraction image (c) at low concentration, the pixel value of the blood vessel image (e) is decreased, and if the user wants to display the blood vessel appeared in the subtraction image (c) at high concentration, the pixel value of the blood vessel image (e) is increased. Therefore, in the fourth embodiment similar to the second embodiment, display concentration of the blood vessel on the subtraction image (c) is changed to suitable concentration.

When the X-ray image generation unit 103 finishes generation of the roadmap image (g) and manipulation to the object begins, the X-ray imaging apparatus 1 captures the live image (b) of the object P in manipulation. Capturing the live image (b) is performed using the same imaging position as that of the contrast-enhanced image (a) and a mask image (d). The imaging control unit 101 captures the live image (b) which is a moving image on real time basis to the object in which the device is inserted, and outputs the live image (b) to the memory unit 106 one after another. Therefore, the live image (b) changes every moment according to movement of the object itself due to, for example, movement of the device inserted into the object and motion of the object.

Next, the image-processing unit 103 performs the subtraction processing to the captured roadmap image (g) and the captured live image (b) to generate a subtraction image (c), and outputs the subtraction image (c) to the memory unit 106. A background, such as a bone, which is captured in common with the roadmap image (g) and the live image (b), is deleted by the subtraction processing, and the subtraction image (c) includes the blood vessel which is captured in the roadmap image (g) with the changed concentration and the device which is captured in the live image (b) to be overlapped each other. The subtraction image (c) changes according to the live image (b) which changes every moment according to the positional relationship between the object and the device.

When the image-processing unit 103 generates the subtraction image (c), the image-processing unit 103 outputs the subtraction image (c) to the display unit 107. The user of the X-ray imaging apparatus 1 confirms the subtraction image (c) displayed on the display unit 107 by sight, and performs manipulation, checking the position of the device in a blood vessel.

Figure 14:
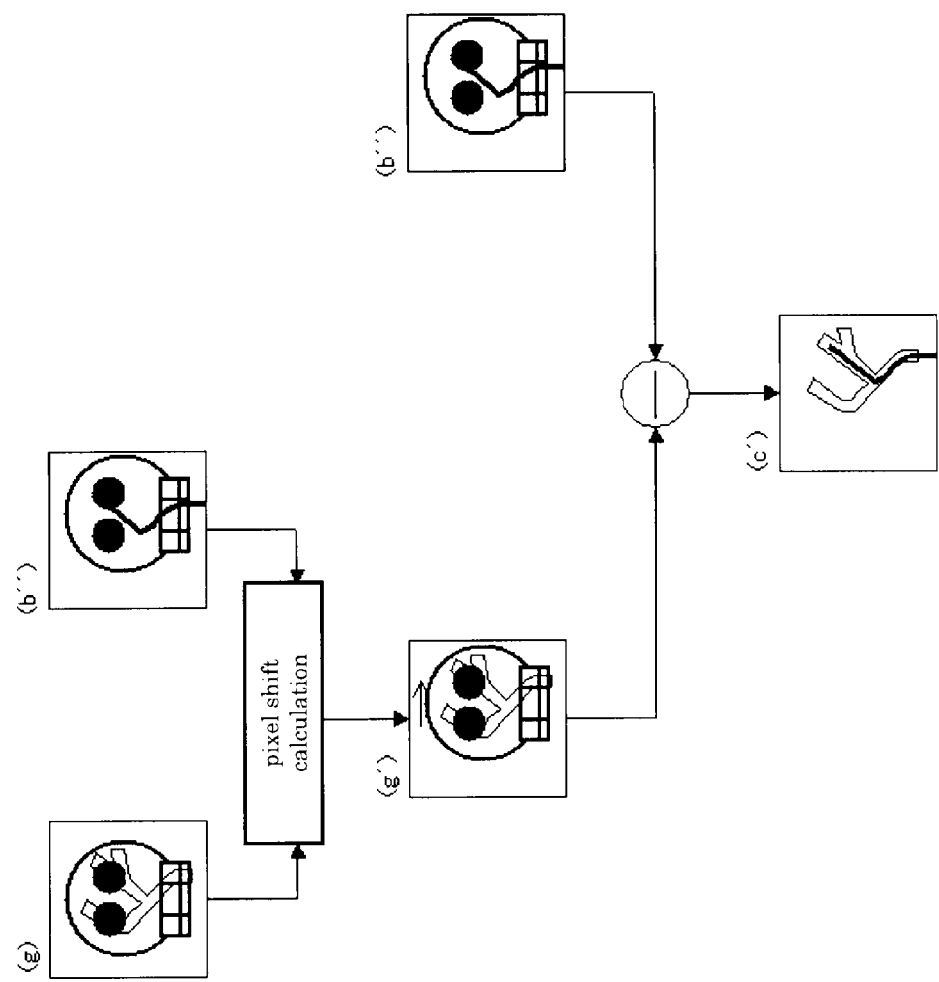
FIG. 14 is a view showing generation processing of the subtraction image using a pixel shift according to the fourth embodiment of the present invention.

By the above processing, the image-processing unit 103 generates the subtraction image (c). When the object moves by motion etc., the subtraction image (c) includes motion artifact. In the fourth embodiment, the subtraction image (c') with reduced motion artifact is generated by performing pixel shift processing to the roadmap image (g). With reference to FIG. 14, generation processing of the subtraction image (c') performed by the image-processing unit 103 is described below. In FIG. 14, explanation of generation processing of the roadmap image (g) is omitted for simplicity.

When the object P in manipulation moves during capturing a live image, as mentioned above, the X-ray image generation unit 102 outputs the live image (b") which includes a background moved to a different position from that of the background in the roadmap image (g). The image-processing unit 103 calculates a pixel shift amount using the live image (b") and the roadmap image (g). By calculation of this pixel shift amount, the image-processing unit 103 substantially calculates the direction and distance of the background which moves in the live image (b").

When the image-processing unit 103 generates the direction and distance of pixel shift processing, the image-processing unit 103 generates the roadmap image (g'), to which pixel shift processing is performed, based on the calculated direction and distance. The roadmap image (g') is substantially considered to be moved according to the movement of the object.

When the roadmap image (g') is generated, the image-processing unit 103 performs subtraction processing to the roadmap image (g') and the live image (b") to generate the subtraction image (c'), and outputs the subtraction image (c') to the display unit 107. Since the background and the blood vessel in the roadmap image (g') are moved according to the background in the live image (b"), a background, such as a bone, which is captured in common with the contrast-enhanced image (a') and the live image (b"), is deleted, and the blood vessel, which is the difference between the contrast-enhanced image (a') and the live image (b"), and the device is captured in the subtraction image (c') to be correctly overlapped each other.

By the above processing, the image-processing unit 103 according to the fourth embodiment performs pixel shift processing to the roadmap image to generate the subtraction image with reduced motion artifact. In order to avoid the pressure of the storage capacity of the memory unit 106, even if the mask image and the contrast-enhanced image are deleted from the memory unit 106, it becomes possible to reduce the motion artifact using pixel shift processing based on a roadmap image. Calculation processing of the pixel shift amount according to the fourth embodiment is not limited to this, and the direction and distance of a pixel shift may be calculated based on other image (e.g., a mask image) and the live image in place of the roadmap image.

Other embodiment of the present invention will be apparent to those skilled in the art from consideration of the specification and practice of the invention disclosed herein. It is intended that the specification and example embodiments be considered as exemplary only, with a true scope and spirit of the invention being indicated by the following. For example, the order of the X-ray image capturing processing mentioned in each embodiment, and the order of other processing, such as the subtraction processing, the weighting processing and the pixel shift processing may be changed. Moreover, the imaging positions of the live image, the mask image and the contrast-enhanced image may be the same as mentioned above; however, the imaging position of the live image may be changed suitably according to the amount of movement of, for example, a bed and the object. Further, the X-ray imaging apparatus 1 in each embodiment has the C arm 400; however, the invention is not limited to this. For example, the X-ray tube 301 and the X-ray detector 302 may operate independently, and the X-ray detector 302 and the tabletop 500 may be unified as a bed. Some features described in each embodiment may be deleted. Elements descried in different embodiments may be combined.

What is claimed is:

1. An X-ray imaging apparatus having an X-ray irradiation unit to irradiate an X-ray and an imaging unit to capture an X-ray image based on the X-rays comprising:
    a first subtraction unit configured subtract a first X-ray image captured by the imaging unit from a second X-ray image captured by the imaging unit to generate a first subtraction image showing information on a blood vessel;
    a calculation unit configured to calculate an amount of pixel shift between the first X-ray image captured by the imaging unit and the third X-ray image captured by the imaging unit;
    a second subtraction unit configured to subtract the first X-ray image from the third X-ray image to generate a second subtraction image showing information on an insertion instrument, the first X-ray image being performed with a pixel shift correction based on the amount of pixel shift; and
    a synthetic unit configured to combine the first subtraction image with the second subtraction image to generate a synthetic image by performing the pixel shift correction based on the amount of pixel shift.

2. The apparatus of claim 1, wherein the synthetic unit configured to perform weighting of synthetic processing based on either one of the first subtraction image and the second subtraction image.

3. An X-ray imaging apparatus having an X-ray irradiation unit to irradiate an X-ray and an imaging unit to capture an X-ray image based on the X-ray comprising:
    a first subtraction unit configured subtract a first X-ray image captured by the imaging unit from a second X-ray image captured by the imaging unit to generate a first subtraction image showing information on a blood vessel;
    a second subtraction unit configured to subtract the first X-ray image from the third X-ray image to generate a second subtraction image showing information on an insertion instrument, the third X-ray image being captured by the imaging unit after capturing the first X-ray image;
    a synthetic unit configured to combine the first subtraction image with the second subtraction image to generate a synthetic image;
    a third subtraction unit configured to subtract the synthetic image from the first X-ray image to generate a third subtraction image; and
    a fourth subtraction unit configured to subtract the third subtraction image from the first X-ray image to generate a fourth subtraction image.

4. The apparatus of claim 3, further comprising a deleting unit configured to delete at least one of the second X-ray image, the third X-ray image and the second subtraction image.

5. An X-ray imaging apparatus having an X-ray irradiation unit to irradiate an X-ray and an imaging unit to capture an X-ray image based on the X-rays comprising:
    a pixel shift unit configured to calculate an amount of pixel shift between a first X-ray image captured by the imaging unit without a contrast agent and a second X-ray image captured by the imaging unit with a contrast agent and perform pixel shift correction for the second X-ray image based on the amount of pixel shift; and
    a subtraction unit configured to subtract a first X-ray image captured by the imaging unit from a second X-ray image captured by the imaging unit to generate a first subtraction image showing information on a blood vessel;
    a calculation unit configured to calculate an amount of pixel shift between the first X-ray image captured by the imaging unit and the third X-ray image captured by the imaging unit;
    a second subtraction unit configured to subtract the first X-ray image from the third X-ray image to generate a second subtraction image showing information on an insertion instrument, the first X-ray image being performed with a pixel shift correction based on the amount of pixel shift; and a synthetic unit configured to combine the first subtraction image with the second subtraction image to generate a synthetic image by performing the pixel shift correction based on the amount of pixel shift.

6. The apparatus of claim 5, further comprising an input unit configured to receive an input operation, wherein the pixel shift unit calculate the amount of pixel shift based on the input operation, which is received by the input unit, to stop imaging the first X-ray image.

7. An X-ray imaging apparatus having an X-ray irradiation unit to irradiate an X-ray and an imaging unit to capture an X-ray image based on the X-rays comprising:

a first subtraction unit configured to subtract a first X-ray image captured by the imaging unit from a second X-ray image captured by the imaging unit to generate a first subtraction image showing information on a blood vessel;

a synthetic unit configured to combine the first X-ray image with the first subtraction image to generate a synthetic image;

a pixel shift unit configured to calculate an amount of pixel shift between the synthetic image and the third X-ray image and perform pixel shift correction for the synthetic image based on the amount of pixel shift, the third X-ray image, the third X-ray image being captured by the imaging unit after capturing the first X-ray image; and a second subtraction unit configured to subtract the synthetic image performed with the pixel shift correction from the third X-ray image to generate a second subtraction image.

8. The apparatus of claim 7, wherein the synthetic unit configured to change a pixel value of the information on a blood vessel in the first subtraction image.

* * * * *